(12) United States Patent
Saladino et al.

(10) Patent No.: US 7,306,629 B2
(45) Date of Patent: Dec. 11, 2007

(54) FEMORAL HEAD ASSEMBLY WITH VARIABLE OFFSET

(75) Inventors: Joseph Saladino, Pflugerville, TX (US); Mark E. Nadzadi, Austin, TX (US); Brian Burkinshaw, Pflugerville, TX (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 10/613,334

(22) Filed: Jul. 3, 2003

(65) Prior Publication Data

US 2005/0004680 A1    Jan. 6, 2005

(51) Int. Cl.
*A61F 2/32* (2006.01)
(52) U.S. Cl. .................. 623/22.45; 623/23.45; 623/22.42; 623/23.14
(58) Field of Classification Search ............ 623/22.42, 623/22.43, 22.45, 23.11, 22.11, 22.15, 23.12, 623/23.14, 23.47, 23.45, 22.44
See application file for complete search history.

(56) References Cited

U.S. PATENT DOCUMENTS

| | | | | |
|---|---|---|---|---|
| 2,765,787 A | * | 10/1956 | Pellet | 623/23.27 |
| 3,102,536 A | * | 9/1963 | Rose et al. | 623/22.4 |
| 4,170,794 A | * | 10/1979 | Zeibig et al. | 623/22.45 |
| 5,108,452 A | * | 4/1992 | DeMane et al. | 623/22.42 |
| 5,246,462 A | * | 9/1993 | Bekki et al. | 623/23.11 |
| 5,358,524 A | * | 10/1994 | Richelsoph | 623/23.47 |
| 5,389,107 A | * | 2/1995 | Nassar et al. | 623/23.17 |
| 6,969,406 B2 | * | 11/2005 | Tornier | 623/19.13 |
| 6,997,958 B2 | * | 2/2006 | Hassler et al. | 623/22.46 |
| 7,044,976 B2 | * | 5/2006 | Meswania | 623/22.45 |
| 2001/0051831 A1 | * | 12/2001 | Subba Rao et al. | 623/22.42 |
| 2004/0002765 A1 | * | 1/2004 | Maroney et al. | 623/19.12 |
| 2004/0193276 A1 | * | 9/2004 | Maroney et al. | 623/19.14 |

FOREIGN PATENT DOCUMENTS

| | | | |
|---|---|---|---|
| DE | 4204979 A1 | * | 2/1992 |
| DE | 42 04 979 A | | 9/1993 |
| DE | 19953918 A1 | * | 11/1999 |
| DE | 199 52 918 A | | 6/2001 |
| DE | 200 22 306 U | | 7/2001 |
| DE | 20022306 U1 | * | 7/2001 |
| EP | 0 201 407 A | | 11/1986 |
| EP | 0 792 628 A | | 9/1997 |
| FR | 2 290 880 A | | 6/1976 |
| FR | 2 574 283 A | | 6/1986 |
| WO | WO 00/40178 | | 7/2000 |

OTHER PUBLICATIONS

Abstract of patent DE 20022306 U1 published Jul. 12, 2001.*
Abstracts and translation of patent DE 4204979 A1 published Sep. 2, 1993.*
Abstracts and translation of patent DE 19952918 A1 published Jun. 13, 2001.*

* cited by examiner

*Primary Examiner*—Paul B. Prebilic
(74) *Attorney, Agent, or Firm*—Baker & Daniels LLP (57) ABSTRACT

A proximal femoral head assembly having a variable offset that is selectively adjustable to conform to various anatomical conditions encountered during a femoral surgical procedure. The assembly includes a femoral head, a neck removeably connectable to the femoral head, and an adjustment mechanism. The adjustment mechanism provides the neck with a plurality of different femoral offsets with respect to a femoral hip stem.

9 Claims, 6 Drawing Sheets

FEMORAL HEAD ASSEMBLY WITH VARIABLE OFFSET

FIELD OF THE INVENTION

The disclosure generally relates to implantable orthopedic prostheses for total hip arthroplasty and, more particularly, to a proximal femoral head assembly having a variable offset that is selectively adjustable to conform to various anatomical conditions encountered during a femoral surgical procedure.

BACKGROUND OF THE INVENTION

During a total hip arthroplasty, a femoral stem is implanted into the intramedullary canal of a femur. After the stem is inserted to the proper depth and orientation, a femoral head or ball is attached to the proximal end of the stem. This head fits into the socket of an acetabular component and provides a joint motion surface for articulation between the femoral prosthesis and acetabulum. A neck or trunion extends between the femoral ball and stem. In many embodiments, this neck generally has a cylindrical configuration with one end connected to the ball and one end connected to the stem.

Several critical features are important to ensure that the femoral hip prosthesis properly functions once implanted in the femur. One of these features is the femoral head "offset." Femoral offset is the horizontal distance from the center of rotation of the femoral head to a line bisecting the long axis of the femur from a standing A-P x-ray. Similarly, the offset of the proximal femoral component of a hip prosthesis is the horizontal distance from the center of rotation of the femoral head to the long axis of the stem.

One important decision that must be made during hip surgery is how much offset should occur between the femoral ball and stem. If the offset does not match the natural anatomical needs of the patient, then the prosthesis can be positioned too far laterally or medially. An unnecessary decrease in offset greatly affects the success and proper function of the hip implant after surgery.

A decrease in femoral offset medially shifts or moves the femur closer to the pelvis. This decrease can result in impingement of the prosthesis for some patients after surgery. A medial shift can also cause soft tissue surrounding the implant to become loose or lax. Impingement and soft tissue laxity can further lead to instability of the implant, subluxation, and even dislocation. As a further disadvantage, when the offset decreases, the abductor muscles utilize a greater force to balance the pelvis. This increase in force creates a discrepancy that may result in a limp for the patient. As another consequence, the resultant force across the hip joint also increases, and this increase can lead to greater polyethylene wear between the femoral ball and prosthetic acetabular component.

In contrast to a decreased offset, an increase in femoral offset laterally shifts or moves the femur farther from the pelvis. In some instances, an increase in offset is desirable. This increase can reduce the risk of impingement and improve soft tissue tension, resulting in a more stable implant. Further, the adductor muscles can be more properly balanced and improve the gait of the patient. Further, proper balance and alignment can lead to less wear and loosening over time.

Manufacturers and designers of femoral hip prosthesis recognize the shortcomings associated with decreased offset and endeavor to match the offset with the anatomical needs of the patient. In order to remedy these shortcomings, femoral hip prostheses are sold with different offsets. The number and degree of different offsets vary between the manufacturers. A typical prosthetic system can include three to five different offsets for each femoral ball size. For example, a manufacturer may provide femoral balls with offsets of −4 mm, 0 mm, +4 mm, +8 mm, and +12 mm. These offsets would be available for five or six different ball sizes. In short, the manufacturer is required to have an inventory of 18 to 30 different femoral heads.

An inventory of femoral heads of this magnitude is enormous. Further, the costs associated with maintaining and distributing this inventory are very great for a company. This large inventory, then, is a clear disadvantage.

As another important disadvantage, manufacturers offer the femoral head offsets in fixed, discrete, large increments. As noted, the offsets, for example, may be offered in increments of 4 mm, such as offsets of −4 mm, 0 mm, +4 mm, +8 mm, and +12 mm. These fixed increments though may not exactly match the anatomical offset that the patient needs. For example, if the patient requires an offset of +6 mm, then the surgeon must choose between an offset of either +4 mm or +8 mm.

It therefore would be advantageous to provide a proximal femoral head having a variable offset that is selectively adjustable to conform to various anatomical conditions encountered during a femoral surgical procedure.

SUMMARY OF THE INVENTION

The present invention is directed to implantable orthopedic prostheses for total hip arthroplasty and, more particularly, to a proximal femoral ball assembly having a variable offset that is selectively adjustable to conform to various anatomical conditions encountered during a femoral surgical procedure.

The femoral ball assembly generally comprises a head, a neck, and an adjustment mechanism. The head has a smooth spherical outer surface that is adapted to engage an acetabular component or native acetabulum. The neck extends outward from the head and removeably connects to the head using a threaded attachment.

The adjustment mechanism provides a variable offset for the femoral ball assembly. More specifically, the adjustment mechanism varies the length that the neck protrudes from the head. As this length increases, the femoral offset correspondingly increases. As this length decreases, the femoral offset correspondingly decreases. One important advantage then is that the surgeon can intra-operatively select from a wide array of femoral offsets. These offsets can be provided with a small number of components. As such, a large, expensive inventory of differently sized femoral balls with different offsets is not necessary.

Another advantage of the present invention is that a plurality of femoral offsets can be offered in small increments. The offsets, for example, can be offered in 1 mm increments. These small increments can be used to more closely match the natural anatomical needs of the patient. Further, these offsets can be offered in a range from about −10 mm to about +10 mm, but a range of up to about +30 mm is within the scope of the invention.

In another embodiment, a femoral ball system is provided. The system has a plurality of differently sized femoral heads and spacers. These heads and spacers can be utilized with a single neck to provide a multitude of femoral offsets with a plurality of differently sized spherical heads or balls.

In yet another embodiment, two separate axes extend through the femoral ball assembly. A first axis or central axis is concentric with the body of the spherical head, and a second axis or eccentric axis is concentric with the threaded bore of the head. This second axis is also concentric with the adjustment mechanism and neck of the femoral ball assembly. These two axes are parallel to each other and form an acute angle with the longitudinal axis of the stem.

DETAILED DESCRIPTION

Figure 1:
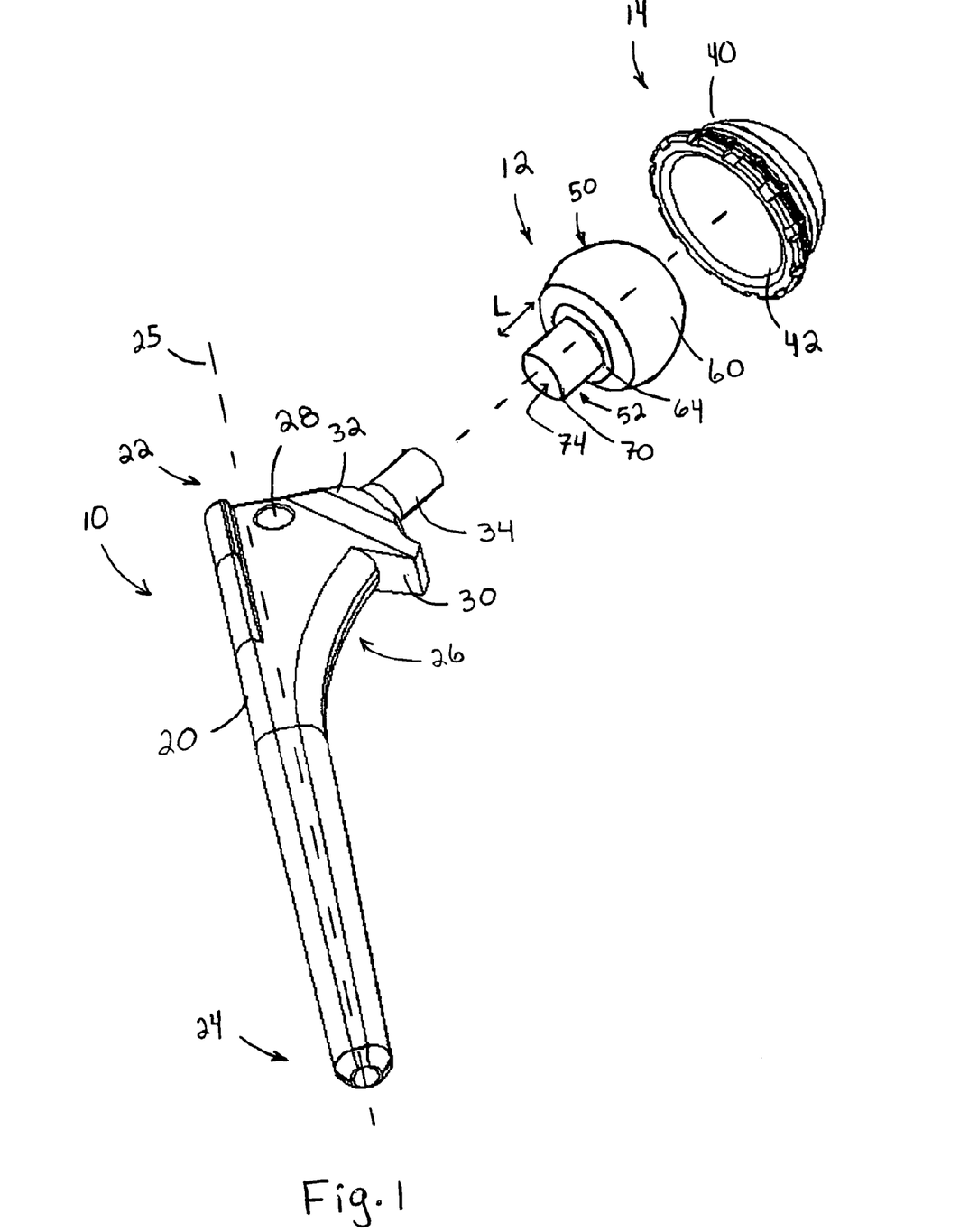
FIG. 1 is an exploded view of a femoral hip stem, an assembled femoral ball assembly according to the invention, and an acetabular component.

Looking to FIG. 1, an implantable orthopedic femoral hip stem or implant 10, a proximal femoral head or ball assembly 12 according to the invention, and an acetabular component 14 are shown. These components are connectable together for use in a total hip arthroplasty.

Stem 10 includes a body 20 that extends from a proximal region 22 to a distal region 24. A longitudinal or long axis 25 extends through the body. The body tapers downwardly and generally has a cylindrical or trapezoidal shape with the distal end being rounded to facilitate insertion into the intramedullary canal of a femur. The proximal region 22 includes a proximal body portion or trochanteral portion 26 having a cylindrical bore 28, a collar 30, and a top surface 32. A neck 34 extends outwardly from the top surface 32. The neck 34 has a tapered body that connects to the femoral ball assembly 12.

The acetabular component 14 is configured to fit in the acetabulum of a patient and is formed from an outer shell 40 and an inner liner or bearing component 42. The shell is generally shaped as a hemispherical cup defined by an outer hemispherical surface or bone engaging surface and an inner hemispherical surface connected to the bearing component. The outer surface can be porous or textured while the inner surface is smooth and adapted to articulate with the femoral ball assembly 12.

One skilled in the art will appreciate that the femoral ball assembly of the present invention can be employed with various implants and implant designs without departing from the scope of the invention. The stem 10, for example, can be the Apollo® Hip or Natural™ Hip manufactured by Centerpulse Orthopedics Inc. of Austin, Tex.; and the acetabular component 14 can be the Allofit™ or Converge™ acetabular system manufactured by the same company.

Figure 2:
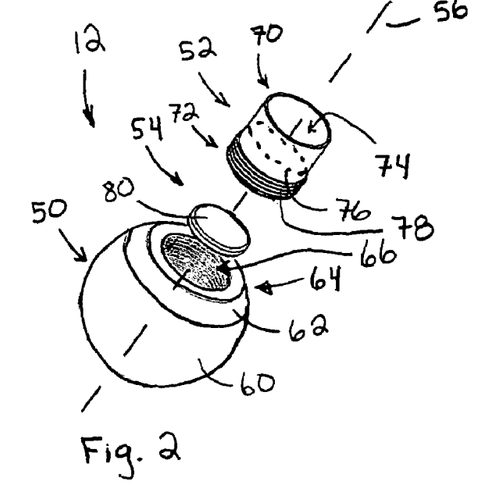
FIG. 2 is an exploded view of the femoral ball assembly according to the invention.

Looking now to FIGS. 1 and 2, the femoral ball assembly 12 is adapted to connect at one end to the femoral hip stem 10 and at another end to the acetabular component 14. The femoral ball assembly 12 comprises a head 50, a neck 52, and an adjustment mechanism 54. A central axis 56 extends through the center of the head, the neck, and adjustment mechanism.

Head 50 has a body that is shaped as a partial sphere. This body has a smooth outer surface 60 adapted to engage and slideably articulate with the bearing component 42 of the acetabular component 14. A collar or tapered transition 62 circumferentially extends around a base 64 of the spherical body. A threaded and cylindrical bore 66 extends into the body.

Neck 52 has a generally straight cylindrically shaped body that extends from a first end 70 to a second end 72. The first end 70 includes a bore 74 adapted to receive and engage neck 34 of stem 10. Specifically, bore 74 has a tapered cylindrical shape with smooth inner walls. This taper is adapted to form a Morse taper connection with neck 34 when stem 10 and femoral ball assembly 12 are connected together. Preferably, bore 74 does not extend completely through neck 52 but stops at a generally planar end surface 76 shown as dashed lines inside the body. The second end 72 includes an externally threaded section 78. This threaded section is adapted to threadably engage with threaded bore 66 of head 50.

Adjustment mechanism 54 is adapted to vary the effective length "L" (shown in FIG. 1) of neck 52 extending outwardly from head 50. Effective length "L" extends from first end 70 to base 64 of the body of the head 50. Adjustment mechanism 54 is further adapted to provide a variable "offset" between the femoral head assembly 12 and femoral stem 10. Femoral offset is the horizontal distance from the center of rotation of the femoral head to a line bisecting the long axis 25 of the femur from a standing A-P x-ray. Similarly, the offset of the proximal femoral component of a hip prosthesis is the horizontal distance from the center of rotation of the femoral head to the long axis of the stem.

As shown in FIG. 2, adjustment mechanism 54 includes a spacer 80. This spacer has a short cylindrical shape and is preferably formed as a solid round or coin-shape. Spacer 80 is adapted to be removeably positioned in bore 66 of head 50.

An adjustment mechanism of the present invention may be used in various ways to provide a variable offset between the femoral head and femoral stem. FIG. 2 shows one example. While spacer 80 is removed from the bore 66, neck 52 can be threadably connected to head 50. Once the neck is fully seated and threaded into bore 66, the neck 52 will have an effective length L1. This length equals the distance from first end 70 to base 64 of head 50. Neck 52 can be removed from head 50 and spacer 80 then placed inside of bore 66. Spacer 80 has a thickness equal to T. With the spacer 80 placed in bore 66, neck 52 can be threadably connected to head 50. Once the neck is fully seated and threaded into bore 66, the neck 52 will have an effective length L2, wherein L2=L1+T. In other words, the spacer lengthens the distance from first end 70 to base 64 an amount equal to its thickness T.

The embodiment in FIG. 2 is able to provide a femoral ball with two different offsets between the femoral head and femoral stem. The length difference between these two offsets depends on the thickness of the spacer. The spacer can be sized to have various thicknesses. As such, the offset can be varied by varying the thickness of the spacer. Further, a plurality of spacers with different thicknesses can be provided. For example, these spacers could have thicknesses with one millimeter increments, such as 1 mm, 2 mm, 3 mm, 4 mm, 5 mm, 6 mm, etc. Other increments, of course, are within the scope of the invention.

FIGS. 1 and 2 show a Morse taper connection between the neck 34 of stem 10 and neck 52 of femoral ball 12. In this connection, neck 52 functions as the female component and neck 34 functions as the male component. One skilled in the art will appreciate that this connection can be altered and still within the scope of the invention. For example, neck 34 can be formed with a bore to function as the female component, and neck 52 can be formed as a solid tapered cylinder to function as the male component. Various types of other connections could also be employed to connect the stem to femoral ball assembly and still remain within the scope of the invention. These connections include, but are not limited to, press-fit connections, locking rings, radial or expandable devices (such as sleeves or collars), nitinol or other superelastic materials, taper connections, locking connections, various polygonal connections (such as triangular, square, hexagonal, or trapezoidal), and the like. In short, various ways can be used to connect the femoral ball 12 to the stem 10.

Figure 3:
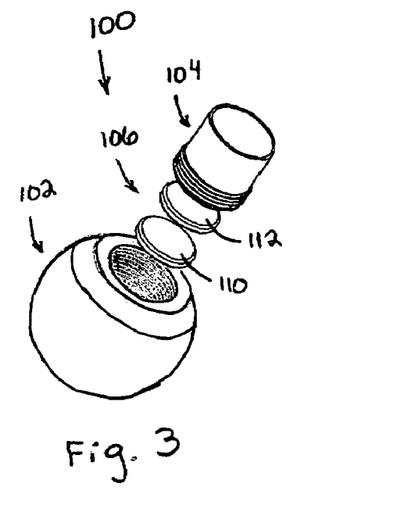
FIG. 3 is an exploded view of an alternate embodiment of the femoral ball assembly.

Looking now to FIG. 3, an alternate femoral ball assembly 100 is shown and includes a head 102, a neck 104, and an adjustment mechanism 106. Head 102 and neck 104 are identical to head 50 and neck 52 described in connection with FIGS. 1 and 2. In FIG. 3, adjustment mechanism 106 includes two spacers 110 and 112. Preferably, these spacers have different thicknesses. These thicknesses, for example, can be selected from a group with one or two millimeter increments, such as 1 mm, 2 mm, 3 mm, 4 mm, 5 mm, 6 mm, etc.

Figure 4:
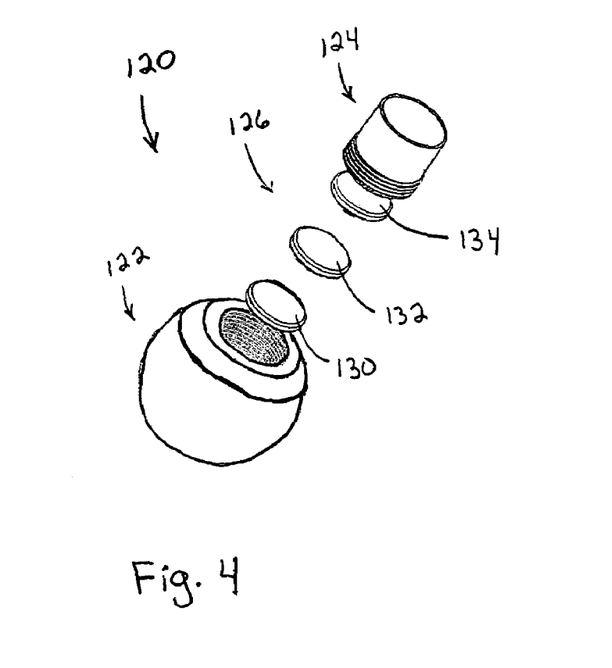
FIG. 4 is an exploded view of an alternate embodiment of the femoral ball assembly.

Looking now to FIG. 4, an alternate femoral ball assembly 120 is shown and includes a head 122, a neck 124, and an adjustment mechanism 126. Head 122 and neck 124 are identical to head 50 and neck 52 described in connection with FIGS. 1 and 2. In FIG. 3, adjustment mechanism 126 includes three spacers 130, 132, and 134. Preferably, these spacers have different thicknesses. These thicknesses, for example, can be selected from a group with one or two millimeter increments, such as 1 mm, 2 mm, 3 mm, 4 mm, 5 mm, 6 mm, etc.

FIGS. 3 and 4 offer a multitude of different offsets between the femoral head and femoral stem. These offsets depend on the number and thickness of spacers used. Further, these spacers can be used alone (i.e., one spacer placed inside the bore of the femoral head) or used in conjunction with other spacers. In the latter scenario, two, three, four, or more spacers can be stacked on top of each other and then placed in the bore of the femoral head. This stacking arrangement can provide a wide range of offsets in small increments. Looking to FIG. 4 to illustrate an example, spacer 130 can have a thickness of 1 mm; spacer 132 can have a thickness of 2 mm; and spacer 134 can have a thickness of 4 mm. These spacers could be used, alone or in stacked combinations with each other, to have thicknesses of 0 mm, 1 mm, 2 mm, 3 mm, 4 mm, 5 mm, 6 mm, or 7 mm. Thus, these three spacers can provide a femoral ball with 8 different offsets, assuming one offset (0 mm) uses no spacer at all.

One advantage of the present invention is that the number and thickness of spacers can vary to provide a multitude of offsets between the femoral head and femoral stem. As another example, four spacers could be provided to have thicknesses of 1 mm, 1 mm, 3 mm, and 6 mm. These four spacers would allow twelve different offset options (0 mm, 1 mm, 2 mm, 3 mm, 4 mm, 5 mm, 6 mm, 7 mm, 8 mm, 9 mm, 10 mm, and 11 mm). This example is illustrated in FIG. 5.

Figure 5:
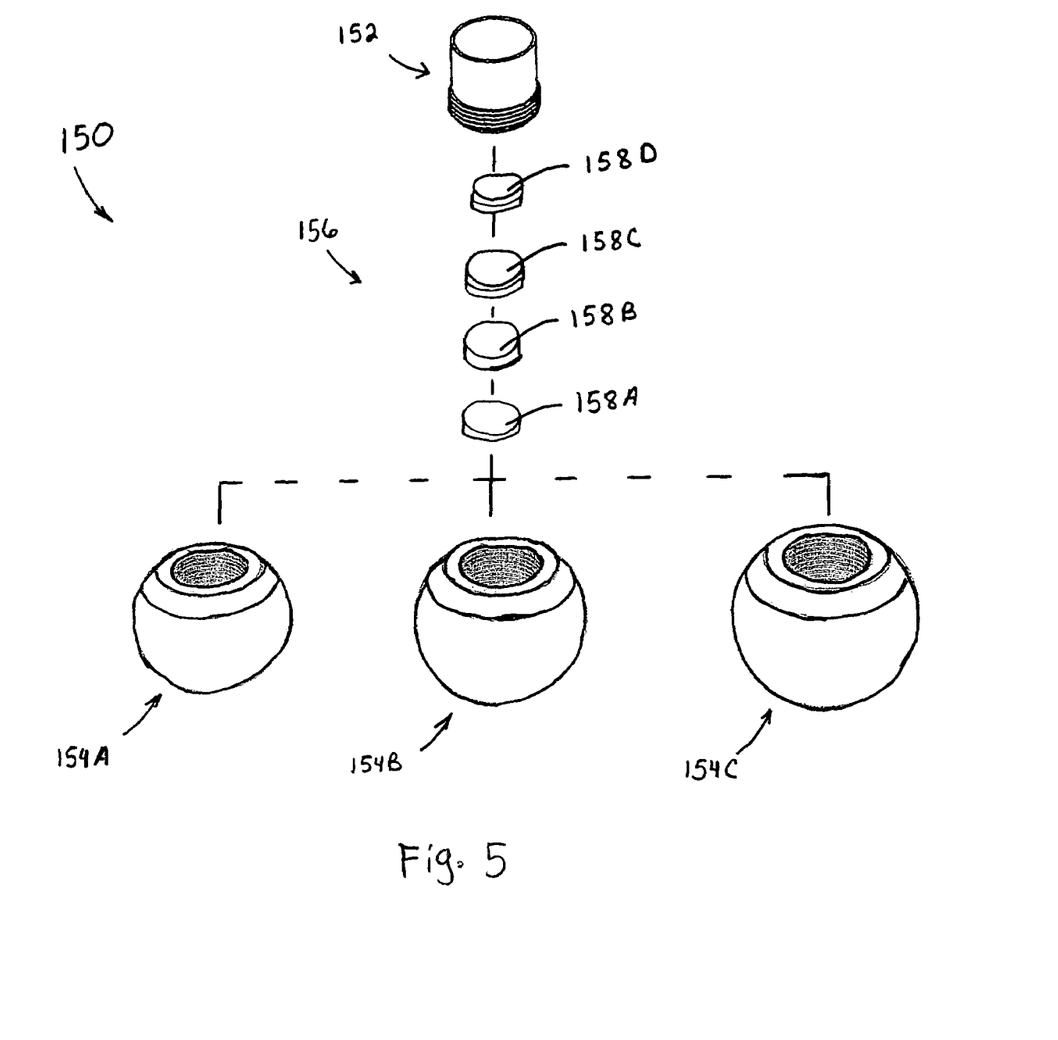
FIG. 5 is an exploded view of a femoral ball system according to the invention.

FIG. 5 shows a femoral ball system 150. System 150 includes a single neck 152, a plurality of femoral heads 154A, 154B, and 154C, and an adjustment mechanism 156 having a plurality of spacers 158A, 158B, 158C, and 158D. The neck, heads, and spacers are generally identical to the neck, head, and spacer discussed in connection with FIGS. 1 and 2. As one difference, the heads and spacers are offered in different sizes. Preferably, each head is sized differently, such as small, medium, and large. More specifically, a plurality of heads could be provided to have outer diameters of 22 mm, 26 mm, 28 mm, 32 mm, 38 mm, and 44 mm. Further, the spacers can be sized to maximize the number of different offsets while reducing the overall number of inventory components. One such size combination is spacers having thicknesses of 1 mm, 1 mm, 3 mm, and 6 mm. One skilled in the art will appreciate that many variations in the number and size of heads and spacers are within th scope of the invention.

Figure 6:
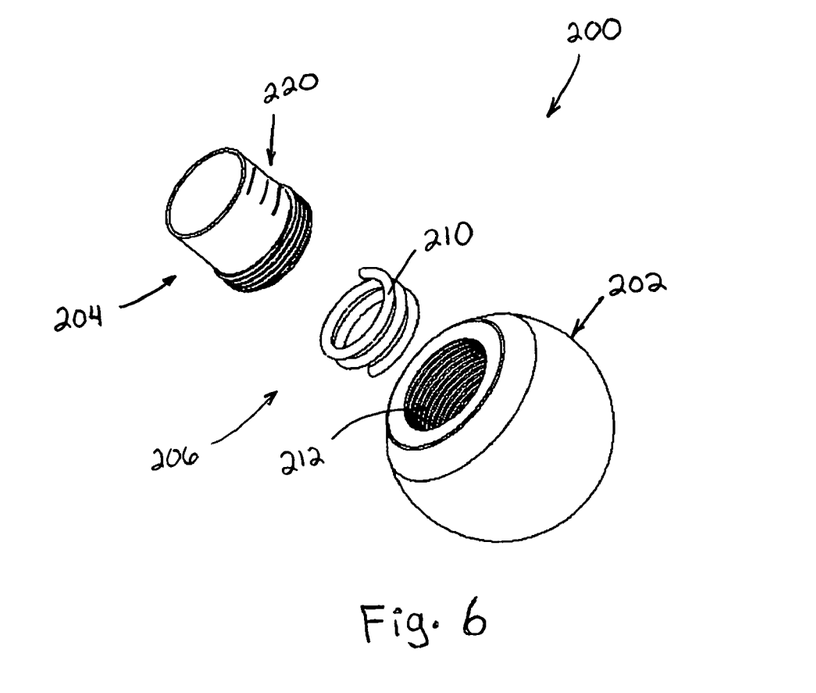
FIG. 6 is an exploded view of an alternate embodiment of the femoral ball assembly.

FIG. 6 shows another embodiment of a femoral ball assembly 200 that includes a head 202, a neck 204, and an adjustment mechanism 206. Head 202 and neck 204 are generally similar to head 50 and neck 52 described in connection with FIGS. 1 and 2. In FIG. 3, adjustment mechanism 206 includes a biasing member 210 that is adapted to be placed into the threaded bore 212 of head 202. Biasing member 210 is shown as a coiled spring, but one skilled in the art will appreciate that many types of biasing members are also available.

During use, the biasing member 210 is placed in bore 212, and then neck 204 is threadably engaged with head 202. As the neck screws into the bore, the biasing member provides a greater and greater force against the neck. In turn, the torque required to screw the neck increases as it threads into the bore. In one embodiment, this torque can be calibrated to specific offset values. In other words, specific torque values can correspond to specific offsets. In another embodiment, indicia or a plurality of calibration marks 220 can be placed on the surface of the neck. Preferably these marks correspond to distinct, finite offsets. Markings could be given to illustrate five different offsets in 4 mm increments, such as −4 mm, 0 mm, +4 mm, +8 mm, and +12 mm. One skilled in the art will appreciate that various indicia can be used to illustrate various offsets.

Figure 7:
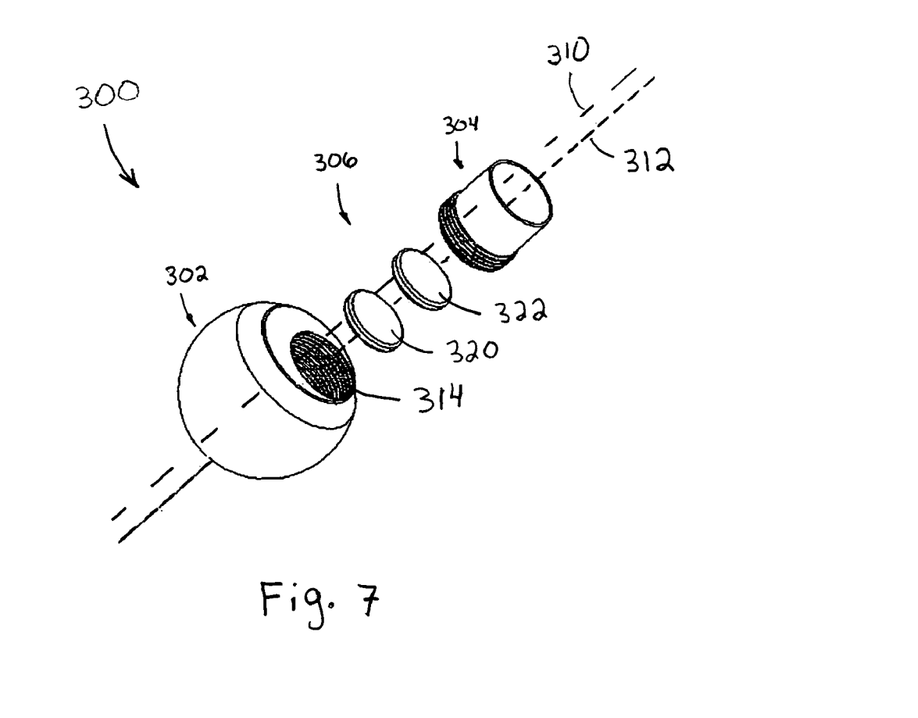
FIG. 7 is an exploded view of another embodiment of the femoral ball assembly.

FIG. 7 shows another embodiment of a femoral ball assembly 300 that includes a head 302, a neck 304, and an adjustment mechanism 306. Neck 304 and adjustment mechanism 306 are identical to the head and adjustment mechanism discussed in connection with FIGS. 1-4. Head 302 is similar to the head 50 discussed in connection with FIGS. 1 and 2 with one important difference: Head 302 is eccentric. More specifically, the body of head 302 has a central axis 310 that passes through the center of the body. The body also has a second or eccentric axis 312 that is parallel to the central axis and passes through the center of threaded bore 314. The center of bore 314 is thus offset or eccentric with the central axis 310 of the body. As shown, the center of spacers 320 and 322 and neck 304 are concentric with bore 314.

The embodiment in FIG. 7 is advantageous because the neck 304 is eccentric or offset from the head 302. This eccentric neck provides an increase range of motion once connected to the femoral hip stem 10 (FIG. 1). This increase in range of motion more fully emulates the anatomical movements of a natural hip. Additionally, this increase in range of motion provides more joint stability to the implanted prosthesis. As yet another advantage, the eccentric neck provides a femoral hip prosthesis that is less likely to experience impingement, subluxation, or even dislocation.

Figure 8:
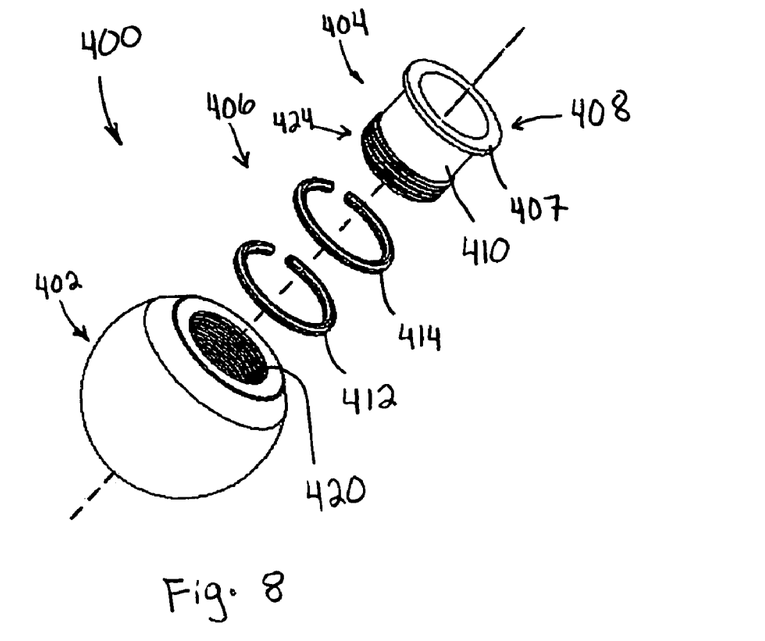
FIG. 8 is an exploded view of yet another embodiment of the femoral ball assembly.
Figure 9:
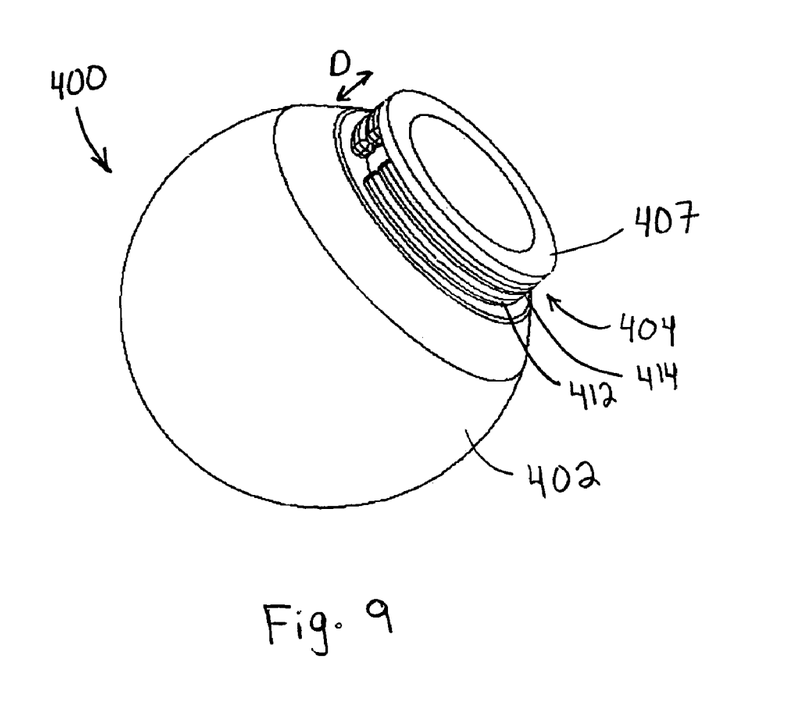
FIG. 9 is an enlarged perspective view of the assembled femoral ball assembly of FIG. 8.

FIGS. 8 and 9 show another embodiment of a femoral ball assembly 400 that includes a head 402, a neck 404, and an adjustment mechanism 406. Head 402 is identical to the head 50 discussed in connection with FIGS. 1 and 2. Neck 404 is similar to the neck 52 discussed in connection with FIGS. 1 and 2 with one important difference: Neck 404 includes a collar or shoulder 407 at first end 408. This collar has a circular or ring-shape and extends outwardly from an outer surface 410 of neck 404.

The adjustment mechanism 406 accomplishes a similar function to the adjustment mechanism 54 discussed in connection with FIGS. 1 and 2, but the function is performed in a different way. More specifically, the adjustment mechanism 406 includes a plurality of spacers 412 and 414. These spacers have a ring-shape or C-clip shape. Unlike spacer 80 in FIGS. 1 and 2, spacers 412 and 414 are not adapted to fit inside bore 420 of head 402. Instead, spacers 412 and 414 are adapted to fit around the second end 424 of neck 404. As best shown in FIG. 9, the spacers extend through second end until they abut against collar 407.

Adjustment mechanism 406 is adapted to vary the effective length of neck 404. As discussed in connection with FIGS. 1 and 2, the adjustment mechanism is further adapted to provide a variable offset between the femoral head and femoral stem. As shown in FIG. 9, the effective length of the neck is increased by a distance "D" equal to the thickness of spacer 412 plus the thickness of spacer 414. These spacers may have equal thicknesses or unequal thicknesses.

FIGS. 8 and 9 show the spacers with a C-clip shape. One skilled in the art will appreciate that other configurations are within the scope of the invention. By way of example, these configurations include a full ring-shape or retaining ring shape.

Figure 10:
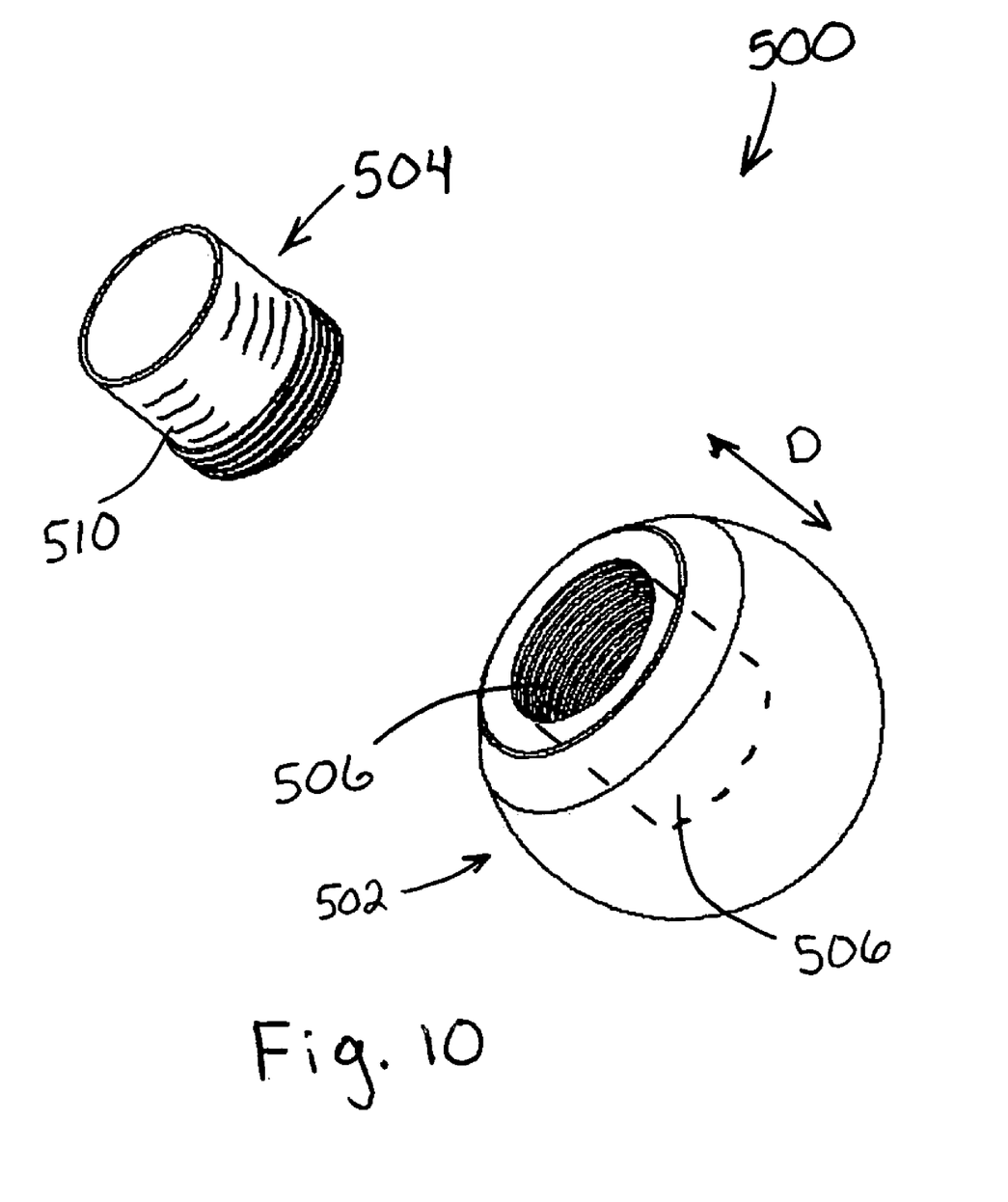
FIG. 10 is an exploded view of another embodiment of the femoral ball assembly.

FIG. 10 shows another embodiment of a femoral ball assembly 500 that includes a head 502 and a neck 504. The head 502 and neck 504 are similarly configured to the head 50 and neck 52 of FIGS. 1 and 2 with several important differences. First, femoral ball assembly 500 does not include a separate adjustment mechanism. Bore 506 has an internally threaded wall that extends along the entire depth of the bore. The neck can thread along the entire length of the bore. Thus, the length of the neck can be varied a distance "D" approximately equal to the depth of the bore. Further, indicia or a plurality of calibration marks 510 can be placed on the outer surface of the neck. Preferably these marks correspond to distinct, finite offsets that the surgeon can view and read during a surgical procedure. Markings could be given to illustrate five different offsets in 4 mm increments, such as −4 mm, 0 mm, +4 mm, +8 mm, and +12 mm. One skilled in the art will appreciate that various indicia can be used to illustrate various offsets and increments.

In order to prevent, the neck from loosening once a desired offset is chosen, a locking mechanism can be used to prevent relative rotational motion between the neck and head.

The femoral head assembly of the present invention may be manufactured of a wide array of biocompatible materials that are known in the art. These materials include ceramics, stainless steel, titanium, and cobalt chrome alloys. Further, the adjustment mechanism may be manufactured from a broader range of materials, such as various elastomers known in the art. Preferably, such an elastomer has a well defined, controlled, and reproducible Poisson's ratio that can be used to adjust and monitor the femoral offset by tightening or loosening the neck to a given load or torque level.

FIGS. 1-9 illustrate a femoral ball assembly wherein the head, neck, and adjustment mechanism are separate components that are removeably connectable to each other. Other embodiments are within the scope of the invention. For example, the adjustment mechanism could be permanently connected to the neck or head. Further, the components can be configured to not be removeable from each other once they are connected. Further yet, the invention can utilize various locking mechanisms to keep or maintain the neck within the head and prevent any unintentional loosening.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. An assembly, comprising a femoral head assembly connectable to a femoral hip stem, the assembly comprising:

a femoral head having a body with a spherical outer surface adapted to articulate within an acetabular component, the body having a threaded bore;

a plurality of spacers of varying thicknesses, at least one of said plurality of spacers adapted to be inserted into the threaded bore;

a first neck having an externally threaded portion and an internal bore, said internal bore having a tapered cylindrical shape, said externally threaded portion being adapted to be threadably engaged with said threaded bore of said body of said femoral head;

wherein the first neck is adapted to extend outwardly from said femoral head in various lengths, wherein each length corresponds to the thickness of said at least one of said plurality of spacers inserted into the threaded bore; and a femoral hip stem, said femoral hip stem comprising a second neck having a tapered outer surface that is adapted to be positioned in said tapered, cylindrical-shaped internal bore in said first neck to thereby form a Morse taper connection.

2. The assembly of claim 1, wherein said thicknesses of said plurality of spacers are provided in increments of 1 mm.

3. The assembly of claim 1 wherein said plurality of spacers have at least three different thicknesses.

4. The assembly of claim 1 wherein multiple spacers are inserted into said threaded bore of said body of said femoral head to vary an offset of said first neck from said femoral head.

5. An assembly, comprising:

a femoral head having a body with an outer surface adapted to articulate with an acetabular component, said femoral head comprising an internally threaded bore;

a first neck having a first externally threaded end adapted to be threadingly connected to the internal threaded bore of said femoral head and a second end comprising a tapered, cylindrical-shaped internal bore;

a femoral hip stem, said femoral hip stem comprising a second neck having a tapered outer surface that is adapted to be positioned in said tapered, cylindrical-shaped internal bore in said first neck to thereby form a Morse taper connection; and at least one spacer adapted to be positioned within said internally threaded bore of said femoral head between said first end of said first neck and said femoral head, wherein said at least one spacer engages said first end of said first neck and a bottom surface of said internally threaded bore of said femoral head when said first neck is threadingly coupled and seated in said internally threaded bore of said femoral head, said first neck extending outwardly from said femoral head by a length that corresponds to a thickness of said at least one spacer positioned within said internally threaded bore.

6. The assembly of claim 5, wherein said at least one spacer comprises a plurality of spacers and wherein one of said plurality of spacers engages said first end of said first neck and another of said plurality of spacers engages said bottom surface of said internally threaded bore, and wherein said first neck extends outwardly from said femoral head by a length that corresponds to a combined thickness of said plurality of spacers positioned within said internally threaded bore.

7. The assembly of claim 5, wherein said at least one spacer adjusts a femoral offset of said femoral head with respect to said femoral hip stem.

8. The assembly of claim 5, wherein at least one spacer has a thickness selected from the group consisting of 1 mm, 2 mm, 3 and 4 mm.

9. The assembly of claim 5, wherein said at least one spacer comprises four spacers with at least three different thicknesses.

* * * * *